United States Patent
Ding

(10) Patent No.: US 7,294,329 B1
(45) Date of Patent: Nov. 13, 2007

(54) POLY(VINYL ACETAL) COATINGS FOR IMPLANTABLE MEDICAL DEVICES

(75) Inventor: Ni Ding, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 696 days.

(21) Appl. No.: 10/199,272

(22) Filed: Jul. 18, 2002

(51) Int. Cl.
*A61K 51/00* (2006.01)
*A61M 36/14* (2006.01)

(52) U.S. Cl. .................. 424/1.65; 424/1.29; 424/1.37; 424/1.11; 424/422; 424/400

(58) Field of Classification Search ............... 424/1.11, 424/1.29, 1.65, 9.1, 9.3, 9.361, 9.4, 9.44, 424/9.5, 9.6, 400, 422, 1.37
See application file for complete search history.

(56) References Cited

U.S. PATENT DOCUMENTS

| | | | |
|---|---|---|---|
| 4,733,665 A | 3/1988 | Palmaz | 128/343 |
| 4,800,882 A | 1/1989 | Gianturco | 128/343 |
| 4,886,062 A | 12/1989 | Wiktor | 128/343 |
| 4,977,901 A | 12/1990 | Ofstead | 128/772 |
| 5,112,457 A | 5/1992 | Marchant | 204/165 |
| 5,328,471 A | 7/1994 | Slepian | 604/101 |
| 5,455,040 A | 10/1995 | Marchant | 424/426 |
| 5,464,650 A | 11/1995 | Berg et al. | 427/2.3 |
| 5,578,073 A | 11/1996 | Haimovich et al. | 623/1 |
| 5,605,696 A | 2/1997 | Eury et al. | 424/423 |
| 5,667,767 A | 9/1997 | Greff et al. | 424/9.411 |
| 5,670,558 A | 9/1997 | Onishi et al. | 523/112 |
| 5,700,286 A | 12/1997 | Tartaglia et al. | 623/1 |
| 5,716,981 A | 2/1998 | Hunter et al. | 514/449 |
| 5,824,049 A | 10/1998 | Ragheb et al. | 623/1 |
| 5,830,178 A | 11/1998 | Jones et al. | 604/49 |
| 5,837,313 A | 11/1998 | Ding et al. | 427/2.21 |
| 5,851,508 A | 12/1998 | Greff et al. | 424/9.411 |
| 5,858,746 A | 1/1999 | Hubbell et al. | 435/177 |
| 5,865,814 A | 2/1999 | Tuch | 604/265 |
| 5,873,904 A | 2/1999 | Ragheb et al. | 623/1 |
| 5,971,954 A | 10/1999 | Conway et al. | 604/96 |
| 5,980,928 A | 11/1999 | Terry | 424/427 |
| 5,980,972 A | 11/1999 | Ding | 427/2.24 |
| 6,015,541 A | 1/2000 | Greff et al. | 424/1.25 |
| 6,042,875 A | 3/2000 | Ding et al. | 427/2.24 |
| 6,051,648 A | 4/2000 | Rhee et al. | 525/54.1 |
| 6,056,993 A | 5/2000 | Leidner et al. | 427/2.25 |
| 6,060,451 A | 5/2000 | DiMaio et al. | 514/13 |
| 6,080,488 A | 6/2000 | Hostettler et al. | 428/423.3 |
| 6,096,070 A | 8/2000 | Ragheb et al. | 623/1 |
| 6,099,562 A | 8/2000 | Ding et al. | 623/1.46 |
| 6,110,188 A | 8/2000 | Narciso, Jr. | 606/153 |
| 6,113,629 A | 9/2000 | Ken | 623/1.1 |
| 6,120,536 A | 9/2000 | Ding et al. | 623/1.43 |
| 6,120,904 A | 9/2000 | Hostettler et al. | 428/423.3 |
| 6,121,027 A | 9/2000 | Clapper et al. | 435/180 |
| 6,129,761 A | 10/2000 | Hubbell | 623/11 |
| 6,153,252 A | 11/2000 | Hossainy et al. | 427/2.3 |
| 6,165,212 A | 12/2000 | Dereume et al. | 623/1.13 |
| 4,733,665 C2 | 1/2002 | Palmaz | 606/108 |

FOREIGN PATENT DOCUMENTS

| | | |
|---|---|---|
| EP | 0 665 023 | 8/1995 |
| EP | 0 970 711 | 1/2000 |
| WO | WO 00/12147 | 3/2000 |
| WO | WO 00/64506 | 11/2000 |
| WO | WO 01/01890 | 1/2001 |

OTHER PUBLICATIONS

Grishina et al, Journal of Photochemistry and Photobiology, A: Chemistry (1995), 92 (3), pp. 223-228.*

* cited by examiner

*Primary Examiner*—Dameron L. Jones
(74) *Attorney, Agent, or Firm*—Squire Sanders Dempsey, L.L.P.

(57) ABSTRACT

A coating for a medical device, particularly for a drug eluting stent, is described. The coating includes a polyacetal-based polymer.

22 Claims, 2 Drawing Sheets

POLY(VINYL ACETAL) COATINGS FOR IMPLANTABLE MEDICAL DEVICES

BACKGROUND OF THE INVENTION

1. Field of the Invention

This invention is directed to coatings for implantable medical devices, such as drug eluting vascular stents.

2. Description of the State of the Art

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to be radially compressed against the atherosclerotic plaque of the lesion to remodel the lumen wall. The balloon is then deflated to a smaller profile to allow the catheter to be withdrawn from the patient's vasculature.

Problems associated with the above procedure include formation of intimal flaps or torn arterial linings which can collapse and occlude the conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining and to reduce the chance of the development of restenosis, a stent is implanted in the lumen to maintain the vascular patency.

Stents are used not only as a mechanical intervention but also as a vehicle for providing biological therapy. As a mechanical intervention, stents act as scaffoldings, functioning to physically hold open and, if desired, to expand the wall of the passageway. Typically, stents are capable of being compressed, so that they can be inserted through small vessels via catheters, and then expanded to a larger diameter once they are at the desired location. Examples in patent literature disclosing stents which have been applied in PTCA procedures include stents illustrated in U.S. Pat. No. 4,733,665 issued to Palmaz, U.S. Pat. No. 4,800,882 issued to Gianturco, and U.S. Pat. No. 4,886,062 issued to Wiktor.

Biological therapy can be achieved by medicating the stents. Medicated stents provide for the local administration of a therapeutic substance at the diseased site. In order to provide an efficacious concentration at the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results. One proposed method for medicating stents involves the use of a polymeric carrier coated onto the surface of a stent. A blend which includes a solvent, a polymer dissolved in the solvent, and a therapeutic substance dispersed in the blend is applied to the stent. The solvent is allowed to evaporate, leaving on the stent surface a coating of the polymer and the therapeutic substance impregnated in the polymer. The embodiments of the invention provide coatings for implantable devices, such as stents, and methods of coating the same.

SUMMARY

According to one embodiment of the present invention, a coating for an implantable medical device, such as a stent, is provided. The coating comprises a polymer having a formula

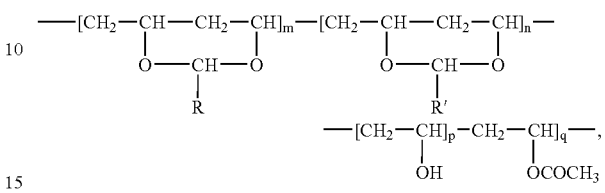

wherein R and R' are each independently selected from a group consisting of hydrogen, a straight-chained or branched alkyl group $C_1$-$C_7$, and an aromatic group, wherein R≠R', and wherein m>0, n≧0, p≧0, and q≧0.

In one embodiment, the coating additionally comprises a therapeutic substance, for example, rapamycin, 40-O-(2-hydroxy)ethyl-rapamycin, 40-O-(3-hydroxy)propyl-rapamycin, 40-O-[2-(2-hydroxy)ethoxy]ethyl-rapamycin, or 40-O-tetrazole-rapamycin.

In accordance with another embodiment, a method of coating an implantable medical device, such as a stent, is provided, comprising depositing the polymer on the device.

In accordance with yet another embodiment, a composition for coating a stent is provided comprising the polymer mixed with a solvent system.

DETAILED DESCRIPTION

Figure 1:
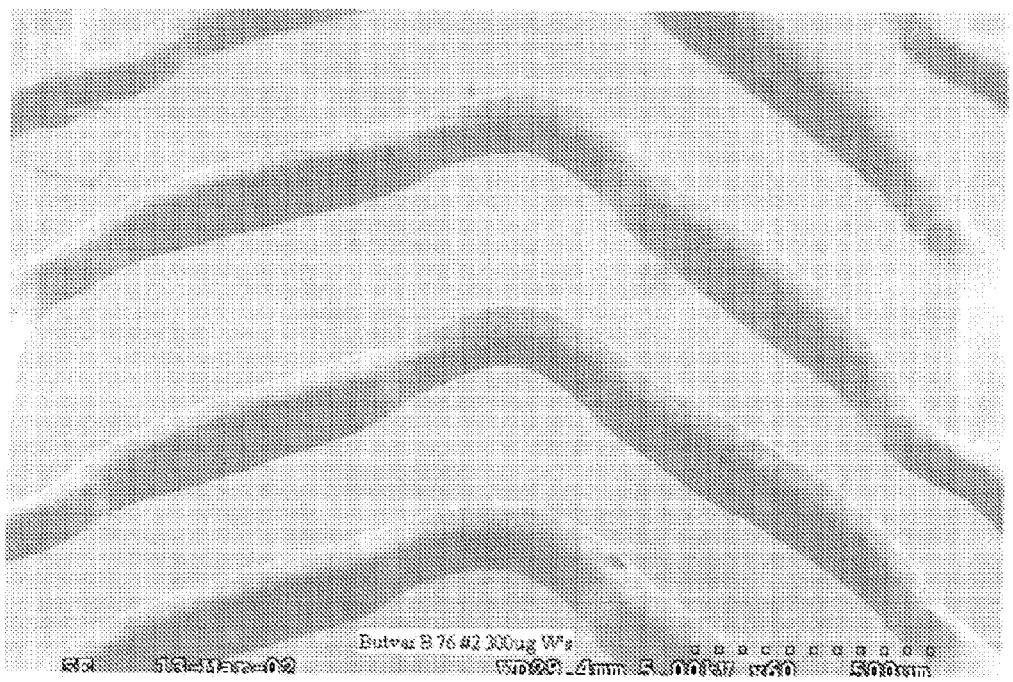
FIGS. 1-3 are scanning electronic micrographs (SEM) showing stents coated with compositions in accordance with some embodiments of the present invention.

A coating for an implantable medical device, such as a stent, according to one embodiment of the present invention, can include a drug-polymer layer or a polymer free drug layer, an optional topcoat layer, and an optional primer layer. The drug-polymer layer or polymer free drug layer can be applied directly onto the stent surface. The topcoat layer, which can be essentially free from any drugs, serves as a rate limiting membrane which further controls the rate of release of the drug. The optional primer layer can be applied on the stent surface to improve the adhesion of the drug-polymer layer or the polymer free drug layer to the stent.

According to one embodiment of the present invention, poly(vinyl acetal-co-vinyl alcohol-co vinyl acetate) having the general formula I:

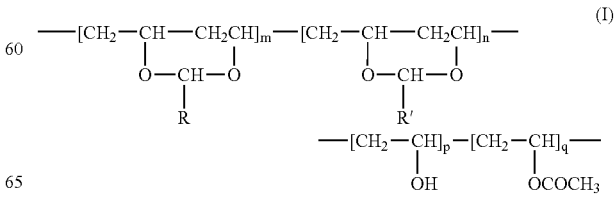

can be used as the coating polymer. In formula (I), R and R' are each, independently, hydrogen, a straight-chained or branched alkyl group $C_1$-$C_7$, or an aromatic group, where R≠R', and each of "m," "n," "p," and "q" is an integer, where m>0, n≧0, p≧0, and q≧0. Examples of R and R' include hydrogen, methyl, ethyl, n-propyl, n-butyl, n-amyl, benzyl, and methylbenzyl groups.

Polymers of formula I can be used for making either the drug-polymer layer, the topcoat layer, the optional primer layer, or any combination thereof. For the purposes of the present invention, such polymers are defined as "polyacetal-based polymers." Typical polyacetal-based polymers that can be used can be terpolymers which are derived from poly(vinyl acetate) (PVA). PVA is hydrolyzed first followed by the process of acetal-formation. The polyacetal-based polymers are formed by reacting the hydrolyzed PVA with a suitable aldehyde. Examples of the aldehydes that can be used include formaldehyde (methanal), acetaldehyde (ethanal), propionaldehyde (propanal), butyraldehyde (butanal), benzaldehyde, or a mixture thereof.

One example of a polyacetal-based polymer suitable for fabricating either the primer layer, the drug-polymer layer or the topcoat membrane is poly(vinyl butyral-co-vinyl alcohol-co-vinyl acetate) (PVB), described by formula (I), where m>0, n=0, p>0, q≧0, and R is a n-propyl radical $C_3H_7$ (—$CH_2$—$CH_2$—$CH_3$). Integers "m," "p," and "q" can be selected such that PVB contains between about 80 and about 88 mass % of the vinyl butyral-derived units, between about 10.5 and about 20 mass % of vinyl alcohol-derived units, and the balance, if any, of the vinyl acetate-derived units.

The weight-average molecular weight of PVB ($M_w$) can be within a range of between about 40,000 and 250,000, for example, between about 150,000 and 180,000. PVB can be optionally sterilized, for example, by using the electronic beam technique known to those having ordinary skill in the art.

PVB is soluble in many common solvents, has good mechanical and physical properties, and adheres well to the underlying stent surface or the primer layer. PVB is manufactured by Monsanto Corp. of St. Louis, Mo. and is available from Solutia, Inc. of St. Louis under the trade name BUTVAR. PVB is obtained by hydrolysis of PVA followed by reaction of the polymeric product of hydrolysis with butyraldehyde. Typical brands of BUTVAR can include:

(1) terpolymer having about 80 mass % of vinyl butyral-derived units, about 19 mass % of vinyl alcohol-derived units, and the balance vinyl acetate-derived units;

(2) terpolymer having about 80 mass % of vinyl butyral-derived units and the balance vinyl alcohol-derived units; and (3) terpolymer having about 88 mass % of vinyl butyral-derived units, about 11 mass % of vinyl alcohol-derived units, and the balance vinyl acetate-derived units.

Other examples of suitable polymers include poly(vinyl formal) and poly(vinyl formal-co-vinyl alcohol-co vinyl acetate) which are products of treatment of hydrolyzed PVA with formaldehyde (R=H). If desired, mixed polyacetal-based polymers can be used, e.g., those described by the formula (I) where n≠0. One example of a suitable mixed polyacetal-based polymer is poly(vinyl butyral-co-vinyl formal-co-vinyl alcohol-co-vinyl acetate), which is a product of treatment of hydrolyzed PVA with a mixture of butyraldehyde and formaldehyde (R=$C_3H_7$, R'=H).

To fabricate the coating, one of the polyacetal-based polymers, or a blend thereof can be applied on the stent using commonly used techniques known to those having ordinary skill in the art. For example, the polyacetal-based polymer can be applied to the stent by dissolving the polymer in a solvent, or a mixture of solvents and applying the resulting solution on the stent by spraying or immersing the stent in the solution.

Representative examples of some suitable solvents include N,N-dimethylacetamide (DMAC), N,N-dimethylformamide (DMF), dimethylsulfoxide (DMSO), dioxane, cyclohexanone, toluene, and blends of xylene with lower alcohols such as methyl alcohol or ethyl alcohol, lower ketones such as acetone or methyl ethyl ketone, lower acetates such as ethyl acetate, and lower ethers such as tetrahydrofuran (THF).

If the polyacetal-based polymer having vinyl alcohol-derived units (i.e., in formula I, p>0) is used to make the stent coating, the polymer can be further optionally modified utilizing the hydroxyl groups of the vinyl alcohol-derived units. One way of modification is by chemically bonding a biologically active agent or agents to the polyacetal-based polymer, thus providing a stent coating with additional therapeutically beneficial properties. Examples of the biologically active agents that can be bonded include polysaccharides (such as sodium hyaluronate or heparin), hydrophilic molecules (such as polyethylene glycol, polyethylene oxide, poly N-vinyl pyrrolidone, poly acrylic acid and derivatives thereof), peptides (such as poly L-, D-, or L,D-arginine having between 5 and 15 repeating units), proteins, genes and DNA. Another way of modifying the polyacetal-based polymer is by-cross-linking the polymer via the hydroxyl groups. For example, the polyacetal-based polymer can be cross-linked using isocyanates, melamines, epoxides, dialdehydes, or phenol resins using synthetic methods known to those having ordinary skill in the art. The topcoat layer which includes the cross-linked polymer may provide additional control of the drug release rate.

Blends of polyacetal-based polymers with polymers other than polyacetal-based polymers can be used to fabricate the coating. Poly(ethylene-co-vinyl alcohol) (EVAL) is one example of a suitable non-polyacetal-based polymer. EVAL, having the general formula —[$CH_2$—$CH_2$]$_x$—[$CH_2$—CH(OH)]$_y$—, where "x" and "y" are each an integer greater than 0, may also include up to 5 molar % of units derived from styrene, propylene and other suitable unsaturated monomers. A brand of copolymer of ethylene and vinyl alcohol distributed commercially under the trade name EVAL by Aldrich Chemical Co., or manufactured by EVAL Company of America of Lisle, Ill., can be used.

The polyacetal-based polymers, or blends thereof with other suitable polymers, can be used to manufacture the primer layer, drug-polymer layer, topcoat membrane, or all three layers. For example, the polyacetal-based polymers can be included in both the drug-polymer layer and the topcoat membrane, but not in the primer layer. Any combination of the three layers can include a polyacetal-based polymer. If a polyacetal-based polymer is used to make only one of the layers, the other layer or layers can be made of an alternative polymer.

Representative examples of other polymers include poly(hydroxyvalerate), poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly(amino acids), cyanoacrylates, poly(trimethylene carbonate), poly(iminocarbonate), co-poly(ether-esters) (e.g. PEO/PLA), polyalkylene oxalates, polyphosphazenes, biomolecules (such as fibrin, fibrinogen, cellulose, starch, collagen and hyaluronic acid), polyurethanes (such as CORETHANE available from Pfizer Corp. of New York or ELASTEON available from AorTech Biomaterials Co. of Chatswood, Australia), silicones, polyesters, polyolefins, polyisobutylene and ethylene-alphaolefin copolymers, acrylic polymers and copolymers (such as poly(butyl methacrylate), poly(ethyl methacrylate) or poly(hydroxyethyl methacrylate)), vinyl halide polymers and copolymers (such as polyvinyl chloride), polyvinyl ethers other than polyacetals, polyvinylidene halides (such as polyvinylidene fluoride and polyvinylidene chloride), polyacrylonitrile, polyvinyl ketones, polyvinyl aromatics (such as polystyrene), polyvinyl esters (such as polyvinyl acetate, acrylonitrile-styrene copolymers, ABS resins, and ethylene-vinyl acetate copolymers), polyamides (such as Nylon 66 and polycaprolactam), alkyd resins, polycarbonates, polyoxymethylenes, polyimides, polyethers, epoxy resins, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

The coating of the present invention has been described in conjunction with a stent. However, the coating can also be used with a variety of other medical devices. Examples of the implantable medical device that can be used in conjunction with the embodiments of this invention include stent-grafts, grafts (e.g., aortic grafts), artificial heart valves, cerebrospinal fluid shunts, pacemaker electrodes, axius coronary shunts and endocardial leads (e.g., FINELINE and ENDOTAK, available from Guidant Corporation). The underlying structure of the device can be of virtually any design. The device can be made of a metallic material or an alloy such as, but not limited to, cobalt-chromium alloys (e.g., ELGILOY), stainless steel (316L), "MP35N," "MP20N," ELASTINITE (Nitinol), tantalum, tantalum-based alloys, nickel-titanium alloy, platinum, platinum-based alloys such as, e.g., platinum-iridium alloy, iridium, gold, magnesium, titanium, titanium-based alloys, zirconium-based alloys, or combinations thereof. Devices made from bioabsorbable or biostable polymers can also be used with the embodiments of the present invention.

"MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

The active agent or the drug can include any substance capable of exerting a therapeutic or prophylactic effect for a patient. The drug may include small molecule drugs, peptides, proteins, oligonucleotides, and the like. The active agent could be designed, for example, to inhibit the activity of vascular smooth muscle cells. It can be directed at inhibiting abnormal or inappropriate migration and/or proliferation of smooth muscle cells to inhibit restenosis.

Examples of drugs include antiproliferative substances such as actinomycin D, or derivatives and analogs thereof. Synonyms of actinomycin D include dactinomycin, actinomycin IV, actinomycin II, actinomycin $X_1$, and actinomycin $C_1$.

The active agent can also fall under the genus of antineoplastic, anti-inflammatory, antiplatelet, anticoagulant, antifibrin, antithrombin, antimitotic, antibiotic, antiallergic and antioxidant substances.

Examples of such antineoplastics and/or antimitotics include paclitaxel, docetaxel, methotrexate, azathioprine, vincristine, vinblastine, fluorouracil, doxorubicin, hydrochloride, and mitomycin.

Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin.

Examples of such cytostatic or antiproliferative agents include angiopeptin, angiotensin converting enzyme inhibitors such as captopril, cilazapril or lisinopril, calcium channel blockers (such as nifedipine), colchicine, fibroblast growth factor (FGF) antagonists, fish oil (ω-3-fatty acid), histamine antagonists, lovastatin (an inhibitor of HMG-CoA reductase, a cholesterol lowering drug), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium.

Other therapeutic substances or agents which may be appropriate include alpha-interferon; genetically engineered epithelial cells; rapamycin and structural derivatives or functional analogs thereof, such as 40-O-(2-hydroxy)ethyl-rapamycin (known by the trade name of EVEROLIMUS available from Novartis) 40-O-(3-hydroxy)propyl-rapamycin and 40-O-[2-(2-hydroxy)ethoxy]ethyl-rapamycin, 40-O-tetrazole-rapamycin; tacrolimus; and dexamethasone.

EXAMPLES

Some embodiments of the present invention are described in the following Examples.

Example 1

A polymer solution containing between about 0.1 mass % and about 15 mass %, for example, about 2.0 mass % of EVAL and the balance, DMAC solvent, can be prepared. The solution can be applied onto a stent to form a primer layer. To apply the primer layer, a spray apparatus, such as an EFD 780S spray nozzle with a VALVEMATE 7040 control system, manufactured by EFD, Inc. of East Providence, R.I. can be used. The EFD 780S spray nozzle is an air-assisted external mixing atomizer. The composition is atomized by air and applied to the stent surfaces. During the process of applying the composition, the stent can be optionally rotated about its longitudinal axis, at a speed of 50 to about 150 rpm. The stent can also be linearly moved along the same axis during the application.

The EVAL solution can be applied to a 13-mm TETRA stent (available from Guidant Corporation) in a series of 10-second passes, to deposit, for example, 10 μg of coating per spray pass. Instead of the 13-mm TETRA stent, another suitable stent can be used, for example, a 12-mm VISION stent (also available from Guidant Corporation). Between the spray passes, the stent can be dried for about 10 seconds using flowing air with a temperature of about 60° C. Six spray passes can be applied, followed by baking the primer layer at about 140° C. for one hour. As a result, a primer layer can be formed having a solids content of about 60 μg.

"Solids" means the amount of the dry residue deposited on the stent after all volatile organic compounds (e.g., the solvent) have been removed.

A drug-containing formulation can be prepared comprising between about 0.1 mass % and about 15 mass %, for example, about 2.0 mass % of EVAL; between about 0.1 mass % and about 2 mass %, for example, about 1.0 mass % of an active agent, for example, EVEROLIMUS (available from Novartis); and the balance, a mixture of solvents, the mixture containing about 80 mass % of DMAC and about 20 mass % of pentane.

In a manner similar to the application of the primer layer, twenty spray passes can be performed, followed by baking the drug-polymer layer at about 60° C. for about 1 hour, to form the drug-polymer layer having a solids content of about 450 µg.

Finally, a topcoat composition to control the drug release rate can be prepared, comprising between about 0.1 mass % and about 15 mass %, for example, about 2.0 mass % PVB and the balance a mixture of solvents containing about 35 mass % acetone, about 30 mass % FLUX REMOVER AMS, and about 35 mass % xylene. Dissolving PVB in the solvent mixture can be achieved by first mixing PVB with acetone, shaking the mix until PVB is fully dissolved in acetone, followed by adding xylene and FLUX REMOVER AMS and shaking the final solution.

BUTVAR 76 grade of PVB can be used, having the number-average molecular weight. $M_n$ of about 49,700 Daltons, weight-average molecular weight. $M_w$ of about 187,200 Daltons, and the polydispersity index $M_w/M_n$ of about 3.76. Molecular weights can be determined using the method of gel permeation chromatography (GPC) known to those having ordinary skill in the art.

FLUX REMOVER AMS is trade name of a solvent manufactured by Tech Spray, Inc. of Amarillo, Tex. comprising about 93.7% of a mixture of 3,3-dichloro-1,1,1,2,2-pentafluoropropane and 1,3-dichloro-1,1,2,2,3-pentafluoropropane, and the balance methanol, with trace amounts of nitromethane.

In a manner similar to the application of the primer layer and the drug-polymer layer, a number of spray passes can be performed followed by final baking at about 70° C. for about 1 hr. As a result, the topcoat membrane can be formed, the membrane having a solids content of about 50 µg.

The coated stents can be optionally mounted on the balloon catheter and sterilized with electronic beam at energy level of 36kGray. The molecular weight of Butvar 76 changed slightly after electronic beam sterilization. $M_n$=47,700 Daltons, $M_w$=161,600 Daltons.

Example 2

A solution of BUTVAR 76 was prepared as described in Example 1. The solution was sprayed on a 13-mm TETRA stent in a series of 10-second passes, to deposit about 30 µg of coating per spray pass. Between the spray passes, the stent was dried for about 10 seconds using room temperature flowing air. Ten spray passes were applied to deposit the total of about 300 µg of the wet coating, followed by baking the coating at about 70° C. for about 1 hour.

The PVB-coated stent was mounted on 4 by 13 mm TETRA balloons and was subjected to a simulated use by expansion to about 4.0 mm. As seen from a microphotograph shown by FIG. 1, the PVB coating showed no visible cracking or delamination, indicating good mechanical properties of the coating.

Example 3

Figure 2:
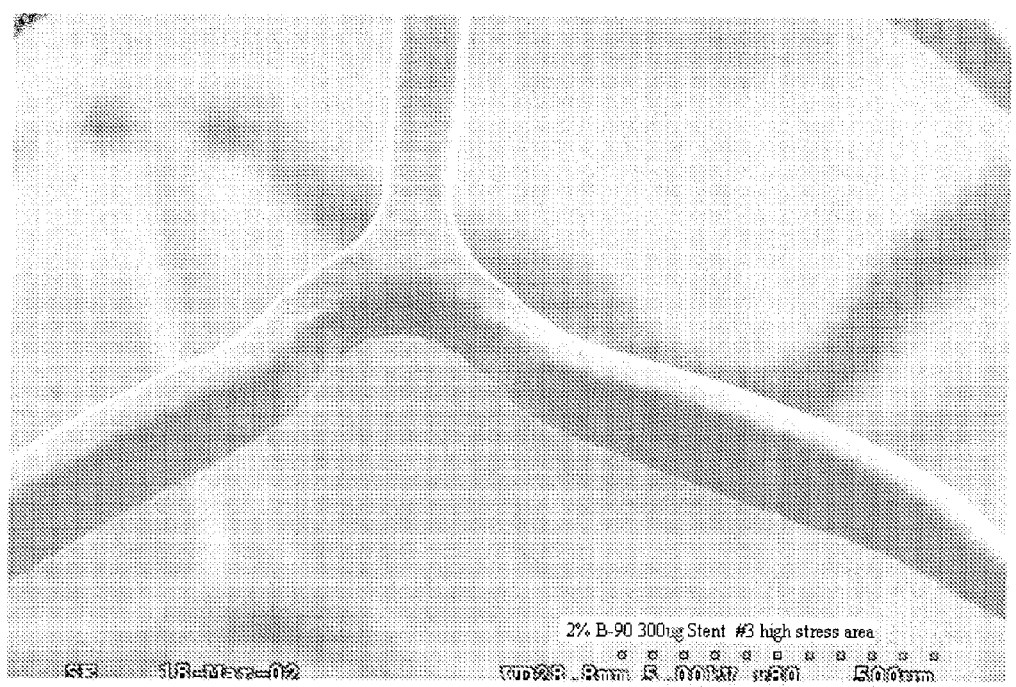

A PVB solution was prepared as described in Example 1, except instead of the BUTVAR 76 grade PVB, BUTVAR 90 grade was used ($M_n$=54,900 Daltons, $M_w$=176,500 Daltons measured by GPC). To dissolve BUTVAR 90, a solvent mixture was used containing about 35 mass % acetone, about 30 mass % FLUX REMOVER AMS, and about 35 mass % cyclohexanone. A stent was coated and subjected to simulated use as described in Example 2. As seen from a microphotograph shown by FIG. 2, the coating showed no visible cracking or delamination.

Example 4

Figure 3:
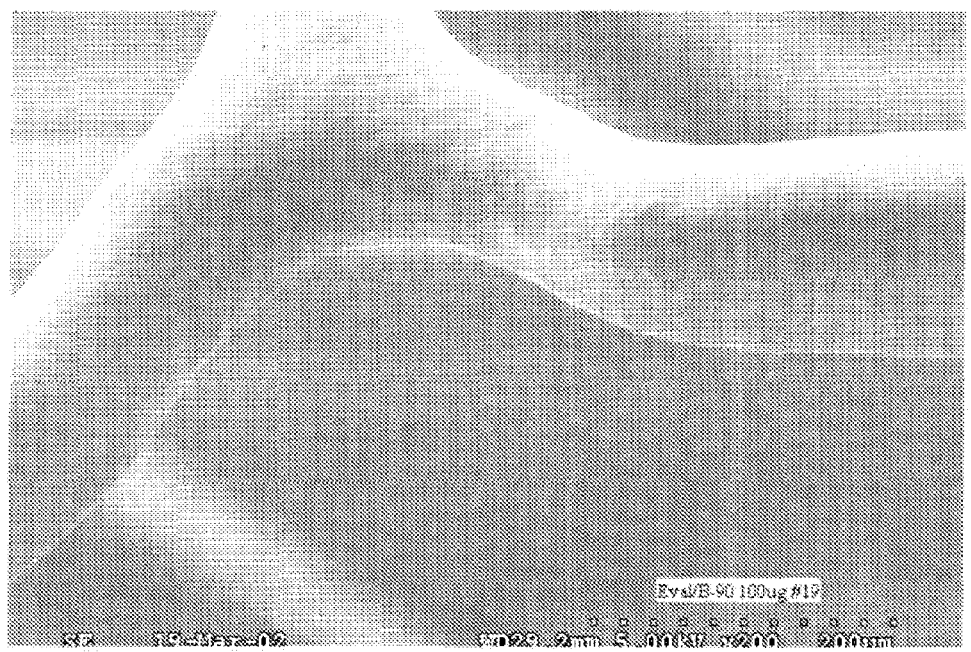

A polymer solution containing about 2.0 mass % of EVAL and the balance, DMAC solvent, was prepared. The EVAL solution was applied to a 13-mm TETRA stent in a series of 10-second passes applying about 10 µg of coating per spray pass to deposit a total of about 300 µg of the wet coating. The wet coating was then dried. The spraying equipment and procedure described in Example 1 was used. A BUTVAR 90 solution was prepared as described in Example 3. The solution was applied over the dried EVAL coating according to the procedure described in Example 2. The PVB-EVAL coated stent was subjected to the simulated use as described in Example 2. As seen from a microphotograph shown by FIG. 3, the coating showed no visible cracking or delamination indicating good adhesion of the overall coating to the stent surface as well as a good adhesion between the layers of the coating.

Example 5

A drug-polymer formulation was prepared comprising about 2.0 mass % of BUTVAR 76; about 1.0 mass % of EVEROLIMUS; and the balance, a mixture of solvents, the mixture containing about 35 mass % acetone, about 30 mass % FLUX REMOVER AMS, and about 35 mass % xylene. Preparing the drug-polymer formulation was achieved by first mixing EVEROLIMUS, BUTVAR 76 and acetone, shaking the mix until EVEROLIMUS and BUTVAR 76 are fully dissolved in the acetone, followed by adding xylene and FLUX REMOVER AMS and shaking the final solution well. The drug-polymer solution was sprayed on a 18-mm VISION stent (available from Guidant Corporation) in a series of 10-second passes. Between the spray passes, the stent was dried for about 10 seconds with room temperature air blow dry. Twenty spray passes were applied to deposit a total of about 600 µg of the wet coating, followed by drying and baking the coating at about 70° C. for about 1 hour.

Example 6

A polymer solution was prepared including about 2.0 mass % BUTVAR 76; and the balance a solvent mixture containing about 35 mass % acetone, about 30 mass % FLUX REMOVER AMS, and about 35 mass % xylene. The solution was applied onto a stent to form a primer layer. The procedure and equipment for fabricating the primer layer described in Example 2 was used. As a result, the primer layer having a solids content of about 60 µg was formed. A drug-polymer formulation was prepared as described in Example 5. The drug-polymer formulation was applied onto the dried BUTVAR 76 primer layer to form the drug-polymer layer. The procedure and equipment described in Example 5 was used for fabricating the drug-polymer layer.

Example 7

A stent was coated as described in Example 6 to form a stent coating having the drug-polymer layer as the outermost layer of the coating. A topcoat layer composition was prepared, the composition comprising about 2 mass % BUTVAR 76 and the balance a solvent mixture containing about 35 mass % acetone, about 30 mass % FLUX REMOVER AMS, and about 35 mass % xylene.

The topcoat formulation was sprayed over the drug-polymer layer to form the topcoat layer having a solids content of about 80 μg. The procedure and equipment described in Example 6 was used to form the topcoat layer.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A coating for an implantable medical device, comprising a polymer having a formula

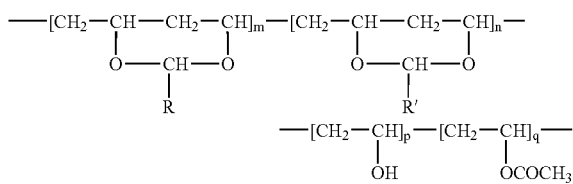

wherein R and R' are each independently selected from a group consisting of hydrogen, a straight-chained or branched alkyl group $C_1$-$C_7$, benzyl, and a methylbenzyl group, wherein R≠R', wherein m>0, n≧0, p>0, and q≧0, and wherein m, n, p, and q are selected so that the polymer has a weight-average molecular weight (Mw) of between about 40,000 and about 250,000 Daltons.

2. A coating for an implantable medical device, comprising a therapeutic substance and a polymer having a formula

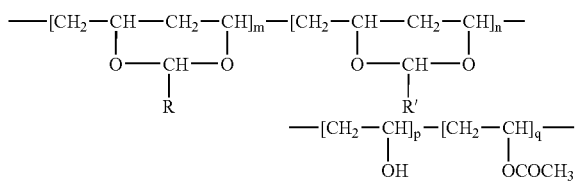

wherein R and R' are each independently selected from a group consisting of hydrogen, a straight-chained or branched alkyl group $C_1$-$C_7$, benzyl, and a methylbenzyl group, wherein R≠R', wherein m>0, n≧0, p≧0, and q≧0, and wherein m, n, p, and q are selected so that the polymer has a weight-average molecular weight (Mw) of between about 40,000 and about 250,000 Daltons.

3. The coating of claim 2, wherein the therapeutic substance is rapamycin, 40-O-(2-hydroxy)ethyl-rapamycin, 40-O-(3-hydroxy)propyl-rapamycin, 40-O-[2-(2-hydroxy)ethoxy]ethyl-rapamycin, or 40-O-tetrazole-rapamycin contained in the coating.

4. The coating of claim 1, wherein the implantable medical device is a stent.

5. A coating for an implantable medical device, comprising a polymer and a biologically active substance bonded to the polymer, the polymer having a formula

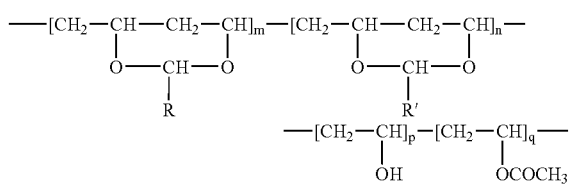

wherein R and R' are each independently selected from a group consisting of hydrogen, a straight-chained or branched alkyl group $C_1$-$C_7$, benzyl, and a methylbenzyl group, wherein R≠R', wherein m>0, n≧0, p≧0%, and q≧0, and wherein m, n, p, and q are selected so that the polymer has a weight-average molecular weight (Mw) of between about 40,000 and about 250,000 Daltons.

6. The coating of claim 5, wherein the biologically active substance is covalently attached to the outermost layer of the coating.

7. The coating of claim 5, wherein the biologically active substance is hyaluronic acid, heparin or a peptide.

8. A coating for an implantable medical device, comprising a polymer having a formula $$—[CH_2—CH—CH_2—CH]_m—[CH_2—CH—CH_2—CH]_n—$$
$$\underset{R}{\overset{O—CH—O}{|}} \quad \underset{R'}{\overset{O—CH—O}{|}}$$
$$—[CH_2—CH]_p—[CH_2—CH]_q—$$
$$\underset{OH}{|} \quad \underset{OCOCH_3}{|}$$

wherein R and R' are each independently selected from a group consisting of hydrogen, a straight-chained or branched alkyl group $C_1$-$C_7$ benzyl, and a methylbenzyl group, wherein R≠R', wherein m>0, n≧0, p≧0, and q≧0, and wherein m, n, p, and q are selected so that the polymer has a weight-average molecular weight (Mw) of between about 40,000 and about 250,000 Daltons, wherein the polymer is cross-linked with a cross-linking agent.

9. The coating of claim 8, wherein the cross-linking agent comprises isocyanates, melamines, epoxides, dialdehydes, or phenol resins.

10. A coating for an implantable medical device, comprising a polymer having a formula $$—[CH_2—CH—CH_2—CH]_m—[CH_2—CH—CH_2—CH]_n—$$
$$\underset{R}{\overset{O—CH—O}{|}} \quad \underset{R'}{\overset{O—CH—O}{|}}$$
$$—[CH_2—CH]_p—[CH_2—CH]_q—$$
$$\underset{OH}{|} \quad \underset{OCOCH_3}{|}$$

wherein R and R' are each independently selected from a group consisting of hydrogen, a straight-chained or branched alkyl group $C_1$-$C_7$, benzyl, and a methylbenzyl group, wherein R≠R', wherein m>0, n≧0, p≧0, and q≧0, wherein m, n, p, and q are selected so that the polymer has a weight-average molecular weight (Mw) of between about 40,000 and about 250,000 Daltons, and wherein the coating additionally comprising a second polymer.

11. The coating of claim 10, wherein the second polymer is poly(ethylene-co-vinyl alcohol).

12. The coating of claim 10, wherein the second polymer is selected from a group consisting of polyacrylates and poly(ethylene vinyl acetate).

13. A coating for an implantable medical device, comprising a polymer having a formula

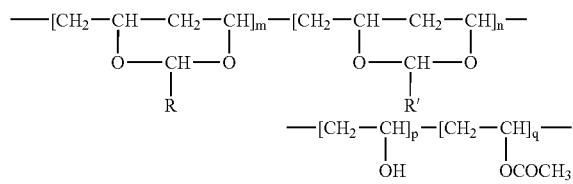

wherein R and R' are each independently selected from a group consisting of hydrogen, a straight-chained or branched alkyl group $C_1$-$C_7$, benzyl, and a methylbenzyl group, wherein R≠R' wherein m>0, n≧0, p≧0, and q≧0, and wherein m, n, p, and g are selected so that the polymer has a weight-average molecular weight (Mw) of between about 40,000 and about 250,000 Daltons, wherein the coating comprises an optional primer layer disposed on the surface of the device, a reservoir layer including a drug for the sustained release of the drug, and an optional topcoat layer disposed over the reservoir layer for reducing the rate of release of the drug, wherein the polymer of claim 1 is at least one or a combination of the layers.

14. A method of coating an implantable medical device, comprising depositing a polymer on the device, the polymer having a formula

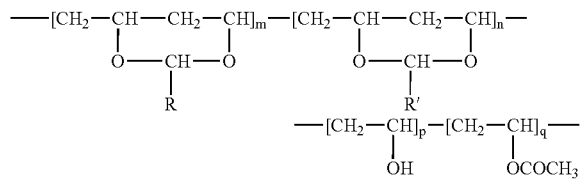

wherein R and R' are each independently selected from a group consisting of hydrogen, a straight-chained or branched alkyl group $C_1$-$C_7$, benzyl, and a methylbenzyl group, wherein R≠R', wherein m>0, n≧0, p≧0, and q≧0, and wherein m, n, p, and q are selected so that the polymer has a weight-average molecular weight (Mw) of between about 40,000 and about 250,000 Daltons.

15. The method of claim 14, wherein the coating additionally includes a therapeutic substance.

16. The method of claim 15, wherein the therapeutic substance is rapamycin, 40-O-(2-hydroxy)ethyl-rapamycin, 40-O-(3-hydroxy)propyl-rapamycin, 40-O-[2-(2-hydroxy)ethoxy]ethyl-rapamycin, or 40-O-tetrazole-rapamycin.

17. The method of claim 14, wherein the implantable medical device is a stent.

18. The method of claim 14, additionally comprising reacting the polymer with a biologically active agent.

19. The method of claim 18, wherein the biologically active agent comprises hyaluronic acid, heparin or a peptide.

20. The method of claim 12, additionally comprising cross-linking the polymer.

21. A composition for coating a stent, comprising a polymer mixed with a solvent system, the polymer having a formula

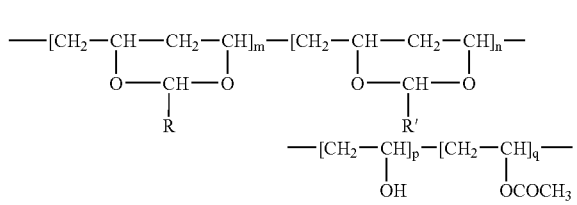

wherein R and R' are each independently selected from a group consisting of hydrogen, a straight-chained or branched alkyl group $C_1$-$C_7$, benzyl, and a methylbenzyl group, wherein R≠R', wherein m>0, n≧0, p>0, and q≧0, and wherein m, n, p, and q are selected so that the polymer has a weight-average molecular weight (Mw) of between about 40,000 and about 250,000 Daltons.

22. A coating for an implantable medical device, comprising a polymer having a formula

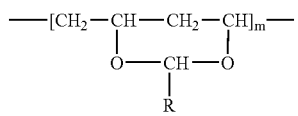

wherein R is $C_4H_9$, and wherein the polymer has a weight-average molecular weight (Mw) of between about 40,000 and about 250,000 Daltons.

* * * * *